(12) United States Patent
Chung et al.

(10) Patent No.: US 8,222,472 B2
(45) Date of Patent: Jul. 17, 2012

(54) METHOD OF PRODUCING 1,3-BUTADIENE FROM N-BUTENE USING CONTINUOUS-FLOW DUAL-BED REACTOR

(75) Inventors: Young Min Chung, Daejeon (KR); Yong Tak Kwon, Daejeon (KR); Tae Jin Kim, Daejeon (KR); Seong Jun Lee, Daejeon (KR); Yong Seung Kim, Seoul (KR); Seung Hoon Oh, Seoul (KR); In Kyu Song, Seoul (KR); Hee Soo Kim, Seoul (KR); Ji Chul Jung, Seoul (KR); Ho Won Lee, Seoul (KR)

(73) Assignees: SK Innovation Co., Ltd. (KR); SNU R&DB Foundation (KR)

( * ) Notice: Subject to any disclaimer, the term of this patent is extended or adjusted under 35 U.S.C. 154(b) by 152 days.

(21) Appl. No.: 12/921,906

(22) PCT Filed: Feb. 9, 2009

(86) PCT No.: PCT/KR2009/000598
§ 371 (c)(1),
(2), (4) Date: Sep. 10, 2010

(87) PCT Pub. No.: WO2009/119975
PCT Pub. Date: Oct. 1, 2009

(65) Prior Publication Data
US 2011/0004041 A1   Jan. 6, 2011

(30) Foreign Application Priority Data

Mar. 28, 2008   (KR) ........................ 10-2008-0029032

(51) Int. Cl.
*C07C 5/333*   (2006.01)

(52) U.S. Cl. ......... 585/616; 585/628; 585/630; 585/631
(58) Field of Classification Search ........................ None
See application file for complete search history.

(56) References Cited

U.S. PATENT DOCUMENTS

| 3,743,683 A | 7/1973 | Croce et al. |
| 3,764,632 A | 10/1973 | Takenaka et al. |
| 3,925,498 A | 12/1975 | Stadig |

(Continued)

FOREIGN PATENT DOCUMENTS

KR   10-2007-0103219   10/2007

(Continued)

OTHER PUBLICATIONS

Luis M. Madeira and Manuel P. Portela, "Catalytic Oxidative Dehydrogenation of n-Butane," Marcel Dekker, Inc., 2002, pp. 247-286.

(Continued)

*Primary Examiner* — Tam M Nguyen
(74) *Attorney, Agent, or Firm* — DLA Piper LLP (US)

(57) ABSTRACT

A method of producing 1,3-butadiene by the oxidative dehydrogenation of n-butene using a continuous-flow dual-bed reactor designed such that two kinds of catalysts charged in a fixed-bed reactor are not physically mixed. More particularly, a method of producing 1,3-butadiene by the oxidative dehydrogenation of n-butene using a C4 mixture including n-butene and n-butane as reactants and using a continuous-flow dual-bed reactor in which a multi-component bismuth molybdate catalyst and a zinc ferrite catalyst having different reaction activity in the oxidative dehydrogenation reaction of n-butene isomers (1-butene, trans-2-butene, cis-2-butene).

14 Claims, 4 Drawing Sheets

U.S. PATENT DOCUMENTS

| | | |
|---|---|---|
| 3,951,869 A | 4/1976 | Baker |
| 3,998,867 A | 12/1976 | Takenaka et al. |
| 2003/0162981 A1 | 8/2003 | Kourtakis et al. |

FOREIGN PATENT DOCUMENTS

| | | |
|---|---|---|
| WO | WO 03/014100 | 2/2003 |
| WO | 2007/119929 A1 | 10/2007 |

OTHER PUBLICATIONS

Michael A. Gibson and Joe W. Hightower, Oxidative Dehyrogenation of Butenes Over Magnesium Ferrite Kinetic and Mechanistic Studies, Journal of Catalysts 41, Inc. 1976, pp. 420-430.

W. Ronald Cares and Joe W. Hightower, "Ferrite Spincis as Catalysts in the Oxidative Dehydrogenation of Butenes," Journal of Catalysts 23, 1971, pp. 193-203.

R.J. Rennard and W. L. Kehl, "Oxidative Dehydrogenation of Butenes Over Ferrite Catalysts," Journal of Catalysts 21, pp. 282-293.

Yu M. Bakshi, R. N. Gur'Yanova, A. N. Mal'yan and A. I. Gel'Bshtein, "Catalytic Properties of System $SnO_2:Sb_2O_4$ in the Oxidative Dehydrogenation of n-Butenes to Butadiene," Petroleum Chemistry, USSR, vol. 7, 1967, pp. 177-185.

A. C. A. M. Bleijenberg, B. C. Lippens and G. C. A. Schuit, "Catalytic Oxidatin of 1-Butene over Bismuth Molybdate Catalyst," Journal of Catalysts 4, 1965, pp. 581-585.

Ph. A. Batist, B. C. Lippens, and G. C. A. Schuit, "The Catalytic Oxidation of 1-Butene over Bismuth Molybdate Catalysts," Journal of Catalysts 5, 1965, pp. 55-64.

W. J. Linn and A. W. Sleight, "Oxidation of 1-Butene over Bismuth Molybdates and Bismuth Iron Molybdate," Journal of Catalysts 41, 1976, pp. 134-139.

Fang-yan Qiu, Lu-Tao Weng, E. Sham, P. Ruiz and B. Delmon, Effect of Added $Sb_2O_4$, $BiPO_4$ or $SnO_2$ on the Catalytic Properties of $ZnFe_2O_4$ in the Oxidative Dehydrogenation of Butene to Butadiene, Applied Catalysis, 51, 1989, pp. 235-253.

J. A. Toledo, P. Bosch, M. A. Valenzuela, A. Montoya and N. Nava, "Oxidative Dehydrogenation of 1-Butene Over Zn-Al Ferrites," Journal of Molecular Catalysis A: Chemical 125, 1997, pp. 53-62.

M. W. J. Woles and PH A. Batist, "The Selective Oxidation of 1-Butene Over a Multicomponent Molybdate Catalyst, Influences of Various Elements on Structure and Activity," Journal of Catalysts, 32, 1974 pp. 25-36.

Wataru eda, Kiyoshi Asakawa, Ching-Ling Chen, Yoshihiko Moro-oka and Tsuneo Ikawa, "Catalytic Properties of Tricomponent Metal Oxides Having the Scheelite Structure," Journal of Catalysts, 101, 1986, pp. 360-368.

L. Marshall Welch, Louis J. Croce and Harold F. Christmann, "Butadiene Via Oxidative Dehydrogenation," Petrochemical Developments, 1978, pp. 59-.

R. K. Grasselli, "Ammoxidation," Handbook of Heterogenous Catalysis, vol. 2, 1997, pp. 2302-2326.

B. Grzybowska, J. Haber and J. Komorek, "The Chemistry of Bi-Mo Oxide Catalysts," Journal of Catalysts, 25, 1972, pp. 25-32.

M. A. Chaar, D. Patel and H. H. Kung, "Selective Oxidative Dehydrogenation of Propane over V-Mg-O Catalysts," Journal of Catalysts, 109, 1988, pp. 463-467.

R. J. Rennard, Jr., R. A. Innes and H. E. Swift, Oxidation over $MgCrFeO_4$ and $ZnCrFeO_4$ Catalysts, Journal of Catalysts, 30, 1973, pp. 128-138.

Yoshihiko Moro-oka and Wataru Ueda, "Multicomponent Bismuth Molybdate Catalyst: A Highly Functionalized Catalyst System for the Selective Oxidation of Olefin," Research Laboratory of Resources Utilization, Tokyo Institute of Technology, Yokohama 227, Japan, 1994, pp. 233-.

Ji Chul Jung, Heesoo Kim, Yong Seung Kim, Young-Min Chung, Tae Jin Kim, Seong Jun Lee, Seung-Hoon Oh and In Kyu Song, Catalytic Performance of Bismuth Molybdate Catalysts in the Oxidative Dehydrogenation of $C_4$ raffinate-3 to 1,3-Butadiene.

Ana Paula Vieira Soares, Lubjmir Dimitrov Dimitrov, Margarida Corte-Real Andre de Oliveira, Leonel Hilaire, Manuel Farinha Portela and Robert Karl Grasselli, "Synergy Effects between β and γ Phases of Bismuth Molybdates in the Selective Catalytic Oxidation of I-Butene," Appllied Catalysis A: General 253, 2003 pp. 191-200.

E.A. Mamedov and V. Cortes Corberan, "Oxidative Dehydrogenation of Lower Alkanes on Vanadim Oxide-Based Catalysts. The Present State of the Art and Outlooks," Applied Catalysis A: General 127, 1995, pp. 1-40.

Wen-Qing Xu, Yuan-Gen Yin, Guo-Ying Li and Shu Chen, Roles of Spinel and Maghemite Phases in the Oxidative Dehydrogenation of Butene over Iron Complex Oxides, II Epitaxy and synergy between $\gamma$-$Fe_2O_3$ and Ferrite Spinels, applied Catalysis A: General, 89, 1992, pp. 131-142.

B.L. Yang, D.S. Cheng and S.B. Lee, "Effect of Steam on the Oxidative Dehydrogenation of Butene Over Magnesium Ferrites with and without Chromium Substitution," Applied Catalysis, 70, 1991, pp. 161-173.

S. Bid and S.K. Pradham, "Preparation of Zinc Ferrite by High-Energy Ball-Milling and Microstructure Characterization by Rietveld's Analysis," Materials Chemistry and Physics 82, 2003, pp. 27-37.

Harold H. Kung and Mayfair C. Kung, "Selective Oxidative Dehydrogenation of Butenes on Ferrite Catalysts," Advances in Catalysis, vol. 33, pp. 159-198.

J.A. Toledo, M.A. Valenzuela, H. Armendraiz, G. Aguilar-Rios, B. Zapata, A. Montoya, N. Nava, P. Salas and I. Schifter, "Oxidative Dehydrogenation of I-Butene to Butadieneon $\alpha$-$Fe_2O_3$/$ZnAl_2O_4$ and $ZnFe_3Al_{2-x}O_4$ Catalysts," Catalysis Letters 30, 1995 pp. 279-288.

Ji Chul Jung, Heesoo Kim, Ahn Seop Choi, Young-Min Chung, Tae Jin Kim, Seong Jun Lee, Seung-Hoon Oh and In Kyu Song, "Effectof pH in the Preparation of $\gamma$-$Bi_2MoO_6$ for Oxidative Dehydrogenation of η-Butene to 1,3-Butadiene: Correlation between Catalytic between Catalytic Performance and Oxygen Mobility of $\gamma$-$Bi_2MoO_6$," Catlysis Communications 8, 2007, pp. 625-628.

Ji Chul Jung, Heesoo Kim, Ahn Seop Choi, Young-Min Chung, Tae Jin Kim, Seong Jun Lee, Seung-Hoon Oh and In Kyu Song, "Preparation, Characterization, and Catalytic Activity of Bismuth Molybdate Catalysts for the Oxidative Dehydrogenation of n-Butene into 1,3-Butadiene," Journal of Molecular Catalysis A: Chemical 259, 2006, pp. 166-170.

METHOD OF PRODUCING 1,3-BUTADIENE FROM N-BUTENE USING CONTINUOUS-FLOW DUAL-BED REACTOR

RELATED APPLICATIONS

This is a §371 of International Application No. PCT/KR2009/000598, with an international filing date of Feb. 9, 2009 (WO 2009/119975 A2, published Oct. 1, 2009), which is based on Korean Patent Application No. 10-2008-0029032 filed Mar. 28, 2008.

TECHNICAL FIELD

The present disclosure relates to a method of producing 1,3-butadiene using a continuous-flow dual-bed reactor. More particularly, the present disclosure relates to a method of producing 1,3-butadiene, in which a multi-component bismuth molybdate catalyst and a zinc ferrite catalyst exhibiting different reaction activities from each other to n-butene isomers (1-butene, trans-2-butene, and cis-2-butene) in the oxidative hydrogenation of n-butene, and then a continuous-flow dual-bed reactor is configured using the catalysts, thus producing high value-added 1,3-butadiene using a low-priced C4 mixture including n-butane, n-butene and the like as reactants without additionally removing n-butane or refining n-butene.

BACKGROUND

The demand and value of 1,3-butadiene, which is used as an intermediate of petrochemical products in the petrochemical market, has been gradually increasing worldwide. Methods of producing 1,3-butadiene may largely include naphtha cracking, direct dehydrogenation of n-butene, and oxidative dehydrogenation of n-butene. Among them, a naphtha cracking process is problematic in that a large amount of energy is consumed due to high reaction temperature and in that a new naphtha cracker must be installed to meet the increased demand for 1,3-butadiene. Further, a naphtha cracking process is problematic in that the naphtha cracking process is not an independent process for producing only 1,3-butadiene, so that the investment and operation for a naphtha cracker cannot be optimally matched with the production and demand of 1,3-butadiene, and other basic fractions besides 1,3-butadiene are excessively produced. Therefore, an independent process for producing only 1,3-butadiene is required. As an alternative of the independent process, there is a method of producing 1,3-butadiene by a hydrogenation reaction of n-butene. The dehydrogenation reaction of n-butene includes a direct dehydrogenation reaction and an oxidative dehydrogenation reaction. Since the direct dehydrogenation reaction of n-butene is an endothermic reaction, it requires high-temperature reaction conditions and thermodynamic low-pressure reaction conditions, and thus the yield of 1,3-butadiene is very low, so that it is not suitable as a commercial process [M. A. Chaar, D. Patel, H. H. Kung, J. Catal., volume 109, page 463 (1988)/E. A. Mamedov, V. C. Corberan, Appl. Catal. A, volume 127, page 1 (1995)/L. M. Madeira, M. F. Portela, Catal. Rev., volume 44, page 247 (2002)].

Therefore, an oxidative dehydrogenation reaction of n-butene is gradually considered as an effective alternative which is an independent process and can flexibly cope with the change in a situation of the market of 1,3-butadiene. The oxidative dehydrogenation reaction of n-butene, which is a reaction obtaining 1,3-butadiene and water by reacting n-butene with oxygen, is thermodynamically advantageous because stable water is formed as a reaction product. Further, the oxidative dehydration of n-butene is advantageous compared to the direct dehydration of n-butene in that a high yield of 1,3-butadiene can be obtained even at low reaction temperature because the oxidative dehydration of n-butene is an exothermic reaction, whereas the direct dehydration of n-butene is an endothermic reaction, and in that it can be commercially used because it does not need an additional heat supply. Therefore, a process of producing 1,3-butadiene using the oxidative dehydrogenation reaction of n-butene can become an effective independent process capable of satisfying the increasing demand for 1,3-butadiene. In particular, the process of producing 1,3-butadiene using the oxidative dehydrogenation reaction of n-butene is advantageous in that, in the case where a catalyst which can obtain a high yield of 1,3-butadiene even when a C4 mixture including impurities, such as n-butane and the like, is used as a reactant, a C4 raffinate-3 mixture or a C4 mixture can be practically used as a supply source of n-butene, and thus a cheap surplus C4 fraction can be made into high value-added products.

As described above, since the oxidative dehydrogenation reaction of n-butene is a reaction obtaining 1,3-butadiene and water by reacting n-butene with oxygen and has many advantages compared to other processes for producing 1,3-butadiene, it can become an alternative for producing only 1,3-butadiene. Nevertheless, many side reactions, such as complete oxidation and the like, are expected to occur because oxygen is used as a reactant in the oxidative dehydrogenation reaction of n-butene, so that it is most important to develop a catalyst which can maintain high activity by controlling oxidation capacity, suppress side reactions to the highest degree and increase the selectivity of 1,3-butadiene.

Up to date, examples of catalysts used the oxidative dehydrogenation of n-butane include bismuth molybdate-based catalysts [A. C. A. M. Bleijenberg, B. C. Lippens, G. C. A. Schuit, J. Catal., volume 4, page 581 (1965)/Ph. A. Batist, B. C. Lippens, G. C. A. Schuit, J. Catal., volume 5, page 55 (1966)/M. W. J. Wolfs, Ph. A. Batist, J. Catal., volume 32, page 25 (1974)/W. J. Linn, A. W. Sleight, J. Catal., volume 41, page 134 (1976)/W. Ueda, K. Asakawa, C.-L. Chen, Y. Moro-oka, T. Ikawa, J. Catal., volume 101, page 360 (1986)/J. C. Jung, H. Kim, A. S. Choi, Y.-M. Chung, T. J. Kim, S. J. Lee, S.-H. Oh, I. K. Song, J. Mol. Catal. A, volume 259, page 166 (2006) Y. Moro-oka, W. Ueda, Adv. Catal., volume 40, page 233 (1994)/R. K. Grasselli, Handbook of Heterogeneous Catalysis, volume 5, page 2302 (1997)]; ferrite-based catalysts [R. J. Rennard, W. L. Kehl, J. Catal., volume 21, page 282 (1971)/W. R. Cares, J. W. Hightower, J. Catal., volume 23, page 193 (1971)/M. A. Gibson, J. W. Hightower, J. Catal., volume 41, page 420 (1976)/H. H. Kung, M. C. Kung, Adv. Catal., volume 33, page 159 (1985)/J. A. Toledo, M. A. Valenzuela, H. Armendariz, G. Aguilar-Rios, B. Zapzta, A. Montoya, N. Nava, P. Salas, I. Schifter, Catal. Lett., volume 30, page 279 (1995)]; tin-based catalysts [Y. M. Bakshi, R. N. Gur'yanova, A. N. Mal'yan, A. I. Gel'bshteirt, Petroleum Chemistry U.S.S.R., volume 7, page 177 (1967)]; and the like.

The reaction mechanism of the oxidative dehydrogenation reaction of n-butene has been never accurately known, but it is known that C—H bonds are cut from n-butene and simultaneously the oxidation-reduction reaction of the catalyst itself occurs. Therefore, composite oxide catalysts having a specific crystal structure including metal ions having various oxidation states have been used in the oxidative hydrogenation reaction [W. R. Cares, J. W. Hightower, J. Catal., volume 23, page 193 (1971)]. Therefore, all of the above catalysts are composite oxide catalysts having a specific crystal structure. Among the above catalysts, bismuth molybdate-based catalysts and ferrite-based catalysts were reported to exhibit high activity in the oxidative dehydrogenation reaction of n-butene [F.-Y. Qiu, L.-T. Wong, E. Sham, P. Ruiz, B. Delmon, Appl. Catal, volume 51, page 235 (1989)/B. Grzybowska, J. Haber, J. Komorek, J. Catal., volume 25, page 25 (1972)/J. C. Jung, H. Kim, Y. S. Kim, Y.-M. Chung, T. J. Kim, S. J. Lee, S.-H. Oh, I. K. Song, Appl. Catal. A, volume 317, page 244 (2007)].

Among the composite oxide catalysts used in the oxidative dehydrogenation of n-butene, bismuth molybdate-based catalysts include pure bismuth molybdate catalysts made of only bismuth and molybdenum oxide and multi-component bismuth molybdate catalysts made by adding various metal components to the pure bismuth molybdate catalysts. The pure bismuth molybdate catalysts exist in several phases. It is known that the pure bismuth molybdate catalysts existing in three phases, such as α-bismuth molybdate ($Bi_2Mo_3O_{12}$), β-bismuth molybdate ($Bi_2Mo_2O_9$) and γ-bismuth molybdate ($Bi_2MoO_6$), can be practically used [B. Grzybowska, J. Haber, J. Komorek, J. Catal., volume 25, page 25 (1972)/A. P. V. Soares, L. K. Kimitrov, M. C. A. Oliveira, L. Hilaire, M. F. Portela, R. K. Grasselli, Appl. Catal. A, volume 253, page 191 (2003)/J. C. Jung, H. Kim, A. S. Choi, Y.-M. Chung, T. J. Kim, S. J. Lee, S.-H. Oh, I. K. Song, Catal. Commun., volume 8, page 625 (2007)]. However, a process of producing 1,3-butadiene using a pure bismuth molybdate catalyst by the oxidative dehydrogenation reaction of n-butene is difficult to be commercially used because it is limited to increase the yield of 1,3-butadiene using this process [Y. Moro-oka, W. Ueda, Adv. Catal, volume 40, page 233 (1994)]. Accordingly, in order to increase the activity of a bismuth molybdate catalyst to the oxidative dehydrogenation reaction of n-butene, research into a multi-component bismuth molybdate catalyst including various metal components in addition to bismuth and molybdenum has been made [M. W. J. Wolfs, Ph. A. Batist, J. Catal., volume 32, page 25 (1974)/S. Takenaka, A. Iwamoto, U.S. Pat. No. 3,764,632 (1973)].

Multi-component bismuth molybdate-based catalysts were reported in several documents and patents. Concretely, it was reported in the document [M. W. J. Wolfs, Ph. A. Batist, J. Catal., volume 32, page 25 (1974)] that 1,3-butadiene was obtained in a yield of 69% by performing an oxidative dehydrogenation reaction of n-butene using a composite oxide catalyst composed of nickel, cesium, bismuth and molybdenum at 520° C.; it was reported in the document [S. Takenaka, H. Shimizu, A. Iwamoto, Y. Kuroda, U.S. Pat. No. 3,998,867 (1976)] that 1,3-butadiene was obtained in a maximum yield of 62% by performing an oxidative dehydrogenation reaction of a C4 mixture including n-butane and n-butene using a composite oxide catalyst composed of cobalt, iron, bismuth, magnesium, potassium and molybdenum at 470° C.; and it was reported in the document [S. Takenaka, A. Iwamoto, U.S. Pat. No. 3,764,632 (1973)] that 1,3-butadiene was obtained in a maximum yield of 96% by performing an oxidative dehydrogenation reaction of n-butene using a composite oxide catalyst composed of nickel, cobalt, iron, bismuth, phosphorus, potassium and molybdenum at 320° C.

In a process of producing 1,3-butadiene using the multi-component bismuth molybdate catalysts reported in the above documents and patents, a high yield of 1,3-butadiene is obtained by using 1-butene, which is a n-butene isomer having relatively high reaction activity, as a reactant, or, when a C4 mixture including n-butane and n-butene is used as a reactant, a very complicated multi-component bismuth molybdate catalyst including six or more kinds of metal components combined in a predetermined ratio is used. That is, there is a problem in that metal components must be continuously added in order to increase catalytic activity, so that the structure of a catalyst is very complicated and the mechanism for preparing a catalyst is also complicated, with the result that it is difficult to repeatedly produce a catalyst.

Meanwhile, among the above composite oxide catalysts, other than the bismuth molybdate-based catalysts, the ferrite-based catalysts, which are known to have high activity in the oxidative dehydrogenation reaction of n-butane, have a spinel structure. Specifically, each of the ferrite-based catalysts is represented by $AFe_2O_4$ (A=Zn, Mg, Mn, Co, Cu or the like), and has a crystal structure in which oxygen (O) atoms constitute a cubic crystal, and A and Fe atoms are partially bonded between the oxygen (O) atoms [S. Bid, S. K. Pradhan, Mater. Chem. Phys., volume 82, page 27 (2003)]. This spinel-structured ferrite has an oxidation number of 2 or 3, and can be practically used as a catalyst for an oxidative dehydrogenation reaction for producing 1,3-butadiene from n-butene through the oxidation-reduction of iron ions and the interaction between oxygen ions in crystal and oxygen gases [M. A. Gibson, J. W. Hightower, J. Catal, volume 41, page 420 (1976)/R. J. Rennard, W. L. Kehl, J. Catal., volume 21, page 282 (1971)].

In relation to the oxidative dehydrogenation reaction of n-butene, the practical uses of ferrite-based catalysts were reported in several documents and patents. Concretely, it was reported in the document [R. J. Rennard, W. L. Kehl, J. Catal., volume 21, page 282 (1971)] that 1,3-butadiene was obtained in a yield of 41% by performing an oxidative dehydrogenation reaction of n-butene using a zinc ferrite catalyst, which is prepared by coprecipitation method and has a pure spinel structure, at 375° C.; it was reported in the document [J. A. Toledo, P. Bosch, M. A. Valenzuela, A. Montoya, N. Nava, J. Mol. Catal. A, volume 125, page 53 (1997)] that 1,3-butadiene was obtained in a yield of 21% by performing an oxidative dehydrogenation reaction of 5 mol % of 1-butene (5 mol % oxygen, 90 mol % helium) using a zinc ferrite catalyst at 420° C.; and it was reported in the document [B. L. Yang, D. S. Cheng, S. B. Lee, Appl. Catal. Volume 70, page 161 (1991)] that 1,3-butadiene was obtained in a yield of 47% by performing an oxidative dehydrogenation reaction of 1-butene (1-butene:oxygen:water:helium=2:4:20:38) using a magnesium ferrite catalyst at 450° C. Further, in methods of performing an oxidative dehydrogenation reaction using ferrite-based catalysts, the activity of n-butene in an oxidative dehydrogenation reaction was increased by additionally conducting pre-treatment and post-treatment in which additives are added to the catalyst or by physically mixing the catalyst with metal oxides to allow the catalyst to function as a co-catalyst [F.-Y. Qiu, L.-T. Weng, E. Sham, P. Ruiz, B. Delmon, Appl. Catal., volume 51, page 235 (1989)/L. J. Crose, L. Bajars, M. Gabliks, U.S. Pat. No. 3,743,683 (1973)/J. R. Baker. U.S. Pat. No. 3,951,869 (1976)/W.-Q. Xu, Y.-G. Yin, G.-Y. Li, S. Chen, Appl. Catal. A, volume 89, page 131 (1992)].

In addition to the methods of improving the activity of the ferrite-based catalysts by the methods of preparing the zinc ferrite catalyst through the pre-treatment, post-treatment and physical mixing as attempts to increase the activity of catalyst itself, methods of increasing the activity of a catalyst through the deformation of a spinel structure by partially replacing two-valence zinc cations or three-valence iron cations with other metal cations have been reported. In particular, it is reported in documents [J. A. Toledo, P. Bosch, M. A. Valenzuela, A. Montoya, N. Nava, J. Mol. Catal. A, volume 125, page 53 (1997)/R. J. Rennard Jr., R. A. Innes, H. E. Swift, J. Catal., volume 30, page 128 (1973)] that when a catalyst in which iron, as a three valence cationic component, is partially replaced with chromium or aluminum is used, catalytic activity is increased.

The above ferrite-based catalysts used in the oxidative dehydrogenation of n-butene are single-phase ferrite catalysts or multicomponent ferrite catalysts when other metal oxides acts as co-catalysts, and are prepared by coprecipitation. In methods of preparing a ferrite catalyst by coprecipitation, generally, the ferrite catalyst is synthesized by adding an aqueous solution of metal precursors and iron precursors, the aqueous solution including bivalent cations, to an excessive alkaline solution [L. J. Crose, L. Bajars, M. Gabliks, U.S. Pat. No. 3,743,683 (1973)/J. R. Baker, U.S. Pat. No. 3,951,869 (1976)].

In a process of producing 1,3-butadiene by performing an oxidative dehydrogenation reaction of n-butene using ferrite-based catalysts, pure single-phase ferrite catalysts have low activity compared to multi-component ferrite catalysts [J. A. Toledo, P. Bosch, M. A. Valenzuela, A. Montoya, N. Nava, J. Mol. Catal. A, volume 125, page 53 (1997)/R. J. Rennard Jr., R. A. Innes, H. E. Swift, J. Catal., volume 30, page 128 (1973)]. However, when ferrite catalysts partially substituted with metals or multi-component ferrite catalysts are used, 1,3-butadiene can be produced in a high yield compared to when pure single-phase ferrite catalysts are used. However, the ferrite catalysts partially substituted with metals or multi-component ferrite catalysts are difficult to be used commercially because they cannot be repeatedly prepared. Further, since a C4 mixture, which is a reactant used in the present disclosure, includes various components in addition to n-butane known to deteriorate the activity of a catalyst in the oxidative dehydrogenation reaction of n-butene [L. M. Welch, L. J. Croce, H. F. Christmann, Hydrocarbon Processing, page 131 (1978)], there is a problem in that side reactions may be conducted by various components constituting the multi-component ferrite catalyst.

Accordingly, the present Applicants developed a novel method of preparing a multi-component bismuth molybdate catalyst including only four kinds of metal components without undergoing complicated processes, the multi-component bismuth molybdate catalyst having excellent reproducibility and high activity in the oxidative dehydrogenation reaction of n-butene, and a novel method of preparing a single-phase zinc ferrite catalyst. To date, attempts to maximize the yield of 1,3-butadiene using the synergistic action attributable to the difference in reaction activity between the multi-component bismuth molybdate catalyst and the single-phase ferrite catalyst have never been reported.

SUMMARY

Thus, the present Applicants had continuously done research in order to overcome the above-mentioned conventional problems. As a result, they developed a novel method of preparing a multi-component bismuth molybdate catalyst including only four kinds of metal components without undergoing complicated processes, the multi-component bismuth molybdate catalyst having excellent reproducibility and high activity in the oxidative dehydrogenation reaction of n-butene, and a novel method of preparing a single-phase zinc ferrite catalyst. Moreover, they observed that the developed multi-component bismuth molybdate catalyst and single-phase zinc ferrite catalyst exhibited different characteristics from each other in the oxidative dehydrogenation reaction of n-butene. Concretely, they observed that the reaction activity of the single-phase zinc ferrite catalyst to 2-butene of n-butene isomers in the oxidative dehydrogenation reaction of n-butene is higher than the reaction activity thereof to 1-butene, whereas the reaction activity of the multi-component bismuth molybdate catalyst to 1-butene of n-butene isomers in the oxidative dehydrogenation reaction of n-butene is higher than the reaction activity thereof to 2-butene. A C4 mixture used in the present disclosure chiefly includes n-butane and n-butene, and n-butene includes three isomers (1-butene, trans-2-butene and cis-2-butene). Therefore, the present Applicants have attempted to develop a catalytic reaction process for providing high activity to all n-butene isomers through the synergistic action of the single-phase ferrite catalyst having excellent reaction activity to 2-butene and the multi-component bismuth molybdate catalyst having excellent reaction activity to 1-butene. In order to develop this catalytic reaction process, these two catalysts are applied to a continuous flow reactor, thus completing the present disclosure.

Accordingly, an aspect of the present disclosure is to provide a method of producing 1,3-butadiene using a continuous-flow dual-bed reactor such that the yield of butadiene can be increased by directly using a C4 mixture as a reactant without performing a process of separating n-butane from the C4 mixture or a process of extracting n-butene therefrom because the multi-component bismuth molybdate catalyst and single-phase zinc ferrite catalyst having different reaction characteristics from each other to n-butene isomers are simultaneously used.

Another aspect of the present disclosure is to provide a method of preparing a pure single-phase zinc ferrite catalyst and a multi-component bismuth molybdate catalyst including four kinds of metal components, wherein the pure single-phase zinc ferrite catalyst and multi-component bismuth molybdate catalyst have different reaction characteristics from each other and are charged in a continuous-flow dual-bed reactor for producing 1,3-butadiene.

In order to accomplish the above aspects, the present disclosure provides a method of producing 1,3 butadiene using a continuous-flow dual bed reactor, comprising: a) charging the continuous-flow dual bed reactor with a bismuth molybdate-based first catalyst and a ferrite-based second catalyst layer to form a first catalyst layer and a second catalyst layer such that a quartz layer is disposed between the first and second catalyst layers to separate the first and second catalyst layers; b) passing a reactant including a C4 mixture containing n-butene, air and steam through the catalyst layers of the continuous-flow dual bed reactor to conduct an oxidative dehydrogenation reaction; and c) obtaining 1,3-butadiene by the oxidative dehydrogenation reaction.

In the method, the first catalyst is prepared by: a1) providing a first solution including a metal precursor, having bivalent cations, selected from the group consisting of manganese, cobalt and nickel, an iron precursor, and a bismuth precursor; b1) providing a second solution in which a molybdenum precursor is dissolved; c1) dripping the first solution into the second solution to form a coprecipitation solution; d1) stirring the coprecipitation solution for 1~2 hours and then removing moisture therefrom to obtain a solid sample; and e1) drying the solid sample at 150~200° C. and then heat-treating the dried solid sample at 400~600° C. Further, the second catalyst is prepared by: a2) dissolving a zinc precursor and an iron precursor in distilled water to form an aqueous precursor solution; b2) mixing a sodium hydroxide solution having a molar concentration of 1.5~4.0 M with the aqueous precursor solution to form a mixed solution having a pH of 6~10; c2) filtering the mixed solution to obtain a solid catalyst; d2) drying the solid catalyst at 70~200° C.; and e2) heat-treating the dried the solid catalyst at 350~800° C.

According to the present disclosure, a multi-component bismuth molybdate catalyst including four kinds of metal components and a zinc ferrite catalyst coprecipitated in a pH-adjusted solution, which are catalysts exhibiting high activity in the oxidative dehydrogenation reaction of n-butene, are prepared, and then a continuous-flow dual-bed reactor is configured using the two catalysts to combine the different reaction characteristics of the two catalysts, so that the activity of the two catalysts in the oxidative dehydrogenation reaction of n-butene can be maximized, thus obtaining a high yield of 1,3-butadiene. Here, the continuous-flow dual-bed reactor is advantageous in that it can be directly applied to a commercially available process because 1,3-butadiene can be obtained in a high yield only by physically separating the two catalysts from each other while directly using the existing catalytic reactor used in petrochemical industry without introducing an additional reaction apparatus or changing the existing process.

Further, according to the present disclosure, 1,3 butadiene can be produced by the oxidative dehydrogenation of n-butene included in a C4 mixture containing a large amount of n-butane without removing n-butane from the C4 mixture or separating n-butene therefrom due to the use of the continuous-flow dual-bed reactor.

Further, since a process of producing 1,3-butadiene according to the present disclosure, unlike conventional processes of producing 1,3-butadiene using naphtha cracking, is an independent process of producing only 1,3-butadiene by the oxidative dehydrogenation reaction of n-butene, it can actively cope with the change in demand of 1,3-butadiene, thus enabling 1,3-butadiene to be optimally produced depending on market demand. Further, according to the present disclosure, a C4 mixture or C4 raffinate-3 having a low use value in petrochemical industry can be directly produced into 1,3-butadiene having a high use value, so that cheap C4 fractions can be converted into high value-added products, thereby enlarging the use of petroleum and reducing the consumption of energy.

DETAILED DESCRIPTION

Figure 1:
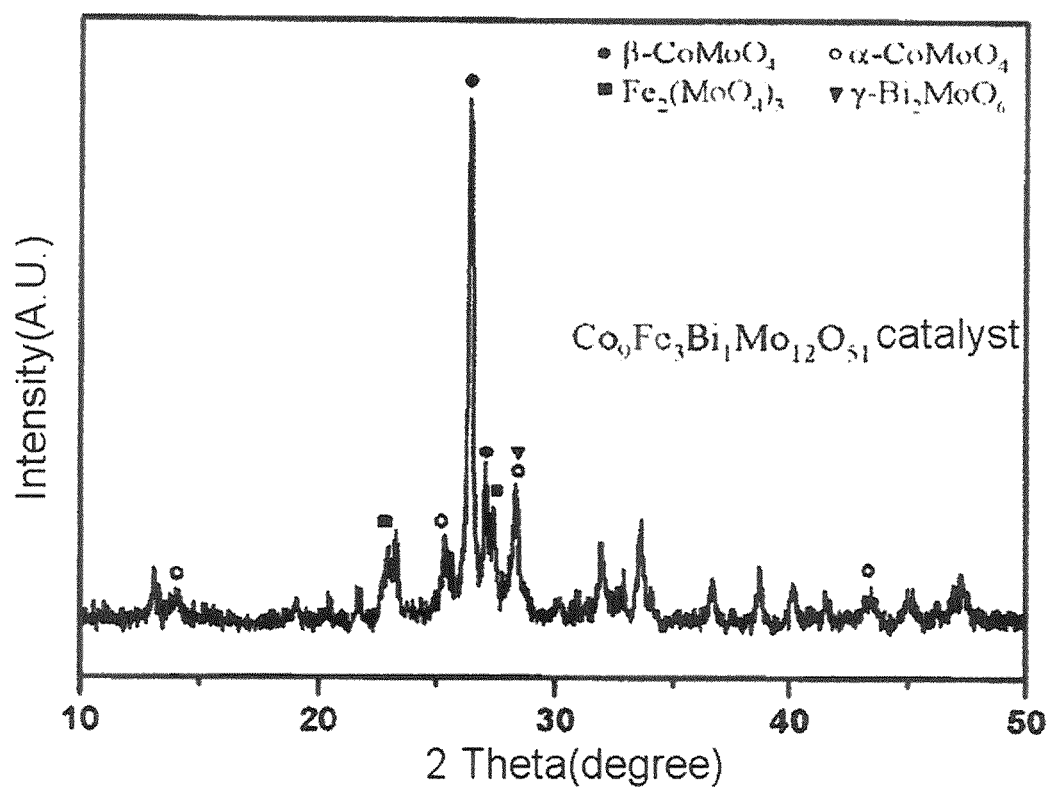
FIG. 1 is a graph showing the result of X-ray diffraction analysis of a multi-component bismuth molybdate catalyst according to Preparation Example 1 of the present disclosure.

Hereinafter, the present disclosure will be described in detail.

As described above, the present disclosure provides a method of producing 1,3-butadiene, in which a multi-component bismuth molybdate catalyst having excellent reproducibility because of its simple components and synthesis path and a zinc ferrite catalyst are prepared by coprecipitation, and then a continuous-flow dual-bed reactor is configured using the two catalysts, and then an oxidative dehydrogenation reaction of n-butene is performed by the continuous-flow dual-bed reactor, thus producing 1,3-butadiene. Further, the present disclosure provides a method of producing 1,3-butadiene in a high yield by using a C4 mixture containing a large amount of n-butane as a reactant without performing a process of removing n-butane from the C4 mixture or a process of separating n-butene therefrom.

The continuous-flow dual-bed reactor for producing 1,3-butadiene can be fabricated by changing the catalyst charging method of a conventional catalytic reactor, and thus can be directly commercially used without performing additional processes. The continuous-flow dual-bed reactor has a dual bed structure including a first catalyst bed made of a multi-component bismuth molybdate-based catalyst and a second catalyst bed made of a ferrite-based catalyst. These two catalysts are charged in a conventional fixed-bed reactor together, and are physically separated from each other by a quartz layer having no reactivity and known as a very stable material even at high temperature, and are thus formed into independent catalyst layers, respectively.

Concretely, the term "C4 mixture" used in the present disclosure is referred to as cheap C4 raffinate-3 remaining after separating useful compounds from a C4 mixture produced by naphtha cracking, and the C4 raffinate-3 is a C4 mixture chiefly including 2-butene (trans-2-butene and cis-2-butene), n-butane and 1-butene.

As the catalysts for producing 1,3-butadiene, which are charged in the continuous-flow dual-bed reactor of the present disclosure in order to obtain 1,3-butadiene in a high yield in the oxidative dehydrogenation reaction, of n-butene, as described above, a multi-component bismuth molybdate catalyst (a first catalyst) containing four kinds of metal component and a pure single-phase zinc ferrite catalyst (a second catalyst) are used.

As described above, the first catalyst, which is a multi-component bismuth molybdate catalyst containing four kinds of metal components, is composed of a metal component having divalent cations, a metal component having trivalent cations, bismuth, and molybdenum. The first catalyst may be formed into various multi-component bismuth molybdate catalysts by controlling the kind of its constituents and the composition ratio thereof. Manganese, cobalt or nickel, preferably, cobalt, may be used as the metal component having divalent cations. According to an embodiment of the present disclosure, the multi-component bismuth molybdate catalyst composed of cobalt, iron, bismuth and molybdenum exhibits the highest activity in the oxidative dehydrogenation reaction of n-butene.

Meanwhile, all kinds of metal precursors for preparing a multi-component bismuth molybdate may be used as long as they are commonly used in the related field. In the present disclosure, cobalt nitrate is used as a precursor of cobalt, iron nitrate is used as a precursor of iron, bismuth nitrate is used as a precursor of bismuth, and ammonium molybdate is used as a precursor of molybdenum. The multi-component bismuth molybdate catalyst can be prepared by changing the composition ratio of the precursors. However, in order to maximize the yield of 1,3-butadiene using the continuous-flow dual-bed reactor, the composition ratio of cobalt/iron/bismuth/molybdenum precursors is adjusted 1~10/1~5/0.1~2/5~20, preferably, 9/3/1/12.

The cobalt, iron and bismuth precursors are simultaneously dissolved in distilled water, and a molybdenum precursor is separately dissolved in distilled water, and then the two precursor solutions are mixed with each other. In this case, in order to increase the solubility of the precursors, an acid solution (for example, a nitric acid solution) etc, may be added. When the precursors are completely dissolved, the precursor solution including cobalt, iron and bismuth is added to the precursor solution including molybdenum to coprecipitate metal components. The mixed solution is stirred for 0.5~24 hours, preferably, 1~2 hours such that metal components are sufficiently coprecipitated. Water and other liquid components are removed from the stirred mixed solution using a vacuum or centrifugal separator, thus obtaining a solid sample. The obtained solid sample is dried for 24 hours at 20~300° C., preferably, 150~200° C. to form a solid catalyst. The formed solid catalyst is put into an electric furnace, and is then heat-treated at 300~800° C., preferably 400~600° C., more preferably 450~500° C., thereby preparing a multi-component bismuth molybdate catalyst.

Meanwhile, the second catalyst is a single-phase zinc ferrite catalyst used to obtain 1,3-butadiene in a high yield in the oxidative dehydrogenation reaction of n-butene, and its catalytic characteristics are changed depending on preparation conditions, and thus its catalytic activity is also changed. The present Applicants made a zinc ferrite catalyst exhibiting high activity in the oxidative dehydrogenation reaction of n-butene by precisely adjusting PH, and found that the activity of the zinc ferrite catalyst in the oxidative dehydrogenation reaction of n-butene is changed depending on the PH of a coprecipitated solution. That is, the second catalyst exhibits excellent activity in the oxidative dehydrogenation reaction of n-butene when the pH of a precipitated solution of a zinc precursor and an iron precursor is adjusted to a range of 6 to 10, preferably 9. In relation to the pH, when the pH of the precipitated solution is less than 6, there is a problem in that α-iron oxide (α-$Fe_2O_3$)(III) having low 1,3-butadiene selectivity is formed, and, when the pH thereof is greater than 10, there is a problem in that the reaction activity of the second catalyst is decreased, thus reducing the yield of 1,3-butadiene. The zinc precursor and iron precursor for preparing the zinc ferrite catalyst may be used without limitation as long as they are commonly used in the related field. Generally, zinc chloride, iron chloride, zinc nitrate and iron nitrate may be used as the zinc precursor and the iron precursor. In the present disclosure, zinc chloride and iron chloride are used as the zinc precursor and the iron precursor.

The amount of the zinc precursor and the iron precursor is adjusted such that the ratio of the number of iron atoms to the number of zinc atoms is in a range of 1.5~2.5, preferably 2, and then the zinc precursor and the iron precursor are dissolved in distilled water to mix them with each other. Here, when the ratio of the number of iron atoms to the number of zinc atoms deviates from the range of 1.5~2.5, it is difficult to introduce zinc atoms into an iron lattice, and catalytic activity becomes low. Meanwhile, in order to coprecipitate zinc ferrite, an aqueous sodium hydroxide solution having a concentration of 1.5~4.0 M, preferably 3 M, is additionally prepared. When the concentration of the aqueous sodium hydroxide solution is below 1.5 M, it is difficult to form a ferrite structure, and, when the concentration thereof is above 4.0 M, it is difficult to remove sodium ions bonded with hydroxyl groups, thus deteriorating catalytic activity.

In order to obtain zinc ferrite from zinc precursor and iron precursor, an aqueous precursor solution is injected into distilled water. In this case, the aqueous precursor solution is injected into distilled water together with the prepared aqueous sodium hydroxide solution while the pH of the aqueous sodium hydroxide solution is maintained constant, so as to form a coprecipitation solution. The coprecipitation solution is maintained at a pH of 6~10, preferably 9, and is stirred for 2~12 hours, preferably, 6~12 hours to be sufficiently coprecipitated. The stirred coprecipitation solution is phase-separated for enough time to precipitate a solid catalyst, and then passes through a pressure-sensitive filter to obtain a solid sample. The obtained solid sample is dried for 16 hours at 70~200° C., preferably, 120~180° C., and then the dried solid sample is put into a electric furnace and then heat-treated at 350~800° C., preferably, 500~700° C. to prepare a pure single-phase zinc ferrite catalyst.

According to the present disclosure, the oxidative dehydrogenation reaction of n-butene is conducted by the processes of: adsorbing n-butene which is a reactant on a catalyst; reacting oxygen existing in the lattice of the catalyst with two hydrogen atoms of the n-butene adsorbed on the catalyst to produce 1,3-butadiene and water; and filling the vacant oxygen sites of the lattice of the catalyst with oxygen which is a reactant. Therefore, the reaction activity of a catalyst is influenced by the sites in which n-butene can be activated by the adsorption of n-butene on the catalyst and is influenced by the properties of oxygen existing in the lattice of the catalyst. For this reason, it can be easily predicted that the multi-component bismuth molybdate catalyst and the zinc ferrite catalyst having different crystal structures are different from each other in the catalytic activities thereof in the oxidative dehydrogenation reaction of n-butene because they are different from each other in the sites in which n-butene can be adsorbed and activated and the properties of oxygen existing in the lattice of the catalyst. In particular, according to an embodiment, the multi-component bismuth molybdate catalyst and the zinc ferrite catalyst exhibit different catalytic activities from each other to isomers of n-butene. Concretely, since the multi-component bismuth molybdate catalyst has good reaction activity to 1-butene among n-butene isomers, it is predicted that its activity to an oxidative dehydrogenation reaction is increased as the content of 1-butene in a C4 mixture is increased. Further, since the zinc ferrite catalyst has good reaction activity to 2-butene among n-butene isomers compared to 1-butene, it is predicted that the oxidative dehydrogenation reaction of 2-butene is predominant compared to the oxidative dehydrogenation reaction of 1-butene when a C4 mixture including both 1-butene and 2-butene is used. Accordingly, the present Applicants predicted that the activity in the oxidative dehydrogenation reaction of n-butene in a C4 mixture can be maximized when two catalysts having different properties from each other with respect to n-butene isomers are simultaneously used, and thus they could produce 1,3-butadiene in a high yield using a continuous-flow dual-bed reactor which can make used of the advantages of the two catalysts according to an embodiment of the present disclosure.

A reactor for attaining the synergetic effect of a multi-component bismuth molybdate catalyst and a zinc ferrite catalyst is largely configured in two manners. First, the two catalysts are mechanically mixed with each other to form a single reaction layer, and then an oxidative dehydrogenation reaction of n-butene is performed in the single reaction layer. Second, the two catalysts are physically separated and charged into a continuous-flow dual-bed reactor, and then an oxidative dehydrogenation reaction of n-butene is performed in the continuous-flow dual-bed reactor. However, it was found from examples of the present disclosure that the physical mixing of the two catalysts is not suitable for accomplishing an aspect of the present disclosure. Therefore, it was verified from examples of the present disclosure that the continuous-flow dual-bed reactor, in which a multi-component bismuth molybdate catalyst and a zinc ferrite catalyst are physically separated to form two independent catalyst layers, is suitable for accomplishing an aspect of the present disclosure.

The continuous-flow dual-bed reactor is configured in two manners in order of charging the two catalysts. In the first manner, the continuous-flow dual-bed reactor is configured such that the oxidative dehydrogenation reaction of n-butene is performed by the zinc ferrite catalyst and then performed by the multi-component bismuth molybdate catalyst. Conversely, in the second manner, the oxidative dehydrogenation reaction of n-butene is performed by the multi-component bismuth molybdate catalyst and then performed by the zinc ferrite catalyst. The two manners will be expected to increase the yield of 1,3-butadiene by the synergetic effect in the oxidative dehydrogenation reaction of n-butene due to the use of the continuous-flow dual-bed reactor. However, it is determined that the manner of configuring the continuous-flow dual-bed reactor can be suitably selected depending on the contents of n-butene isomers (1-butene, trans-2-butene, cis-2-butene). In the present disclosure, it was verified that the continuous-flow dual-bed reactor configured such that the oxidative dehydrogenation reaction of n-butene is performed by the zinc ferrite catalyst and then performed by the multi-component bismuth molybdate catalyst is more suitable than the continuous-flow dual-bed reactor configured such that the oxidative dehydrogenation reaction of n-butene is performed by the multi-component bismuth molybdate catalyst and then performed by the zinc ferrite catalyst. The reason for this is determined because the amount of 2-butene in a C4 mixture used as a reactant of the present disclosure is more than the amount of 1-butene therein. Generally, in the petrochemical industry, the utility value of 1-butene is higher than that of 2-butene, and thus most of C4 mixtures include a larger amount of 2-butene than 1-butene. Therefore, the oxidative dehydrogenation reaction of n-butene may be performed by the zinc ferrite catalyst and then performed by the multi-component bismuth molybdate catalyst, and this fact was verified by examples of the present disclosure. However, in the configuration of the continuous-flow dual-bed reactor to accomplish an aspect of the present disclosure, the order of charging the two catalysts is not limited thereto, and may be changed depending on the content of n-butene isomers in a reactant.

The continuous-flow dual-bed reactor used in the present disclosure may be easily configured without providing additional reaction apparatuses or changing the reactor. That is, the continuous-flow dual-bed reactor, which includes a multi-component bismuth molybdate catalyst layer and a zinc ferrite catalyst layer physically separated from each other, can be configured only by charging a zinc ferrite catalyst, powdered quartz and a multi-component bismuth molybdate layer in order of bringing them into contact with a reactant. Here, the two catalysts are separated from each other by the powdered quartz layer. It is determined that quartz is suitable for physically separating the two catalysts because it is stable and does not react with a C4 mixture even at high temperature. However, in order to accomplish an aspect of the present disclosure, when the continuous-flow dual-bed reactor is configured, since quartz is not necessarily required to separate the two catalyst layers and is used only to physically separate them, other materials or devices which do not influence the reaction of the present disclosure may be used instead of quartz.

Next, the present disclosure provides a method of producing 1,3-butadiene using the continuous-flow dual-bed reactor including a multi-component bismuth molybdate and a zinc ferrite catalyst, wherein 1,3-butadiene is produced by an oxidative dehydrogenation reaction using a C4 mixture or C4 raffinate-3 including a large amount of n-butane as a supply source of n-butene without removing n-butane or refining n-butene.

According to an Experimental Example of the present disclosure, a zinc ferrite catalyst, quartz, and a multi-component bismuth molybdate catalyst were sequentially charged in a straight pyrex reactor in order of bringing them into contact with a reactant, and the straight pyrex reactor was installed in a electric furnace to maintain reaction temperature constant, and a reactant continuously passed through a catalyst layer disposed in the straight pyrex reactor, thus conducting a reaction. In this case, the reaction was conducted at a reaction temperature of 300~600° C., preferably 350~500° C., and more preferably 420° C., and the amount of the catalyst was adjusted such that gas hourly space velocity (GI-ISV) is 50~5000 h−1 preferably 100~1000 h−1, and more preferably 150~500 h−1 based on n-butene. Further, a C4 mixture, air and steam were used as reactants, and the ratio of n-butene:air:steam was adjusted to 1:0.5~10:1~50, and preferably 1:3~4:10~30. In the present disclosure, the amount of a C4 mixture or C4 raffinate-3 used as a supply source of n-butene and the amount of air used as another reactant were precisely adjusted using a mass flow controller. Further, liquid water was vaporized into steam by injecting it using a syringe pump, and then the steam was introduced into the continuous-flow dual-bed reactor. Concretely, the temperature of liquid water was maintained at 150~300° C., preferably 180~250° C., and thus the liquid water introduced into the continuous-flow dual-bed reactor by the syringe pump was instantly vaporized into steam, and then the steam was completely mixed with other reactants (C4 mixture and air) and then passed through the catalyst layer of the continuous-flow dual-bed reactor.

The C4 mixture, which is one of the reactants used in the present disclosure, includes 0.5~50 wt % of n-butane, 40~99 wt % of n-butene, and 0.5~10 wt % of other C4 compounds. Here, examples of the C4 compounds may include iso-butane, cyclobutane, methyl cyclopropane, iso-butene, and the like.

When the zinc ferrite catalyst and the multi-component bismuth molybdate catalyst are simultaneously used by using the continuous-flow dual-bed reactor of the present disclosure, 1,3-butadiene can be produced in a high yield by the oxidative dehydrogenation reaction of n-butene even when a cheap C4 mixture or C4 raffinate-3 including n-butane and n-butene is used as a reactant. Therefore, when the multi-component bismuth molybdate catalyst of the present disclosure is used, the conversion rate of n-butene and the selectivity of 1,3-butadiene can be increased without removing n-butane even when a C4 mixture including 20 wt % or more of n-butane is directly used as a reactant.

Further, since the continuous-flow dual-bed reactor of the present disclosure can be configured only by charging a conventional catalytic reactor with the multi-component bismuth molybdate catalyst and zinc ferrite catalyst separated from each other by quartz without changing the conventional catalytic reactor, it can be easily applied to commercially available processes.

Hereinafter, the present disclosure will be described in more detail with reference to the following Examples. However, the scope of the present disclosure is not limited thereto.

Preparation Example 1

Preparation of a Multi-Component Bismuth Molybdate ($Co_9Fe_3Bi_1Mo_{12}O_{51}$) Catalyst Cobalt nitrate hexahydrate ($Co(NO_3)_2.6H_2O$) was used as a cobalt precursor, iron nitrate nonahydrate ($Fe(NO_3)_3.9H_2O$) was used as an iron precursor, bismuth nitrate pentahydrate ($Bi(NO_3)_2.5H_2O$) was used as a bismuth precursor, and ammonium molybdate tetrahydrate (($NH_4)_6Mo_7O_{24}.4H_2O$) was used as a molybdenum precursor. All of the precursors, except bismuth nitrate pentahydrate, were easily dissolved in distilled water, whereas bismuth nitrate pentahydrate was easily dissolved in a strongly acidic solution. Therefore, bismuth nitrate pentahydrate was separately dissolved in a solution formed by adding nitric acid to distilled water.

In order to prepare a multi-component bismuth molybdate catalyst, the molar ratio of cobalt:iron:bismuth:molybdenum was fixed at 9:3:1:12. 7.94 g of cobalt nitrate hexahydrate ($Co(NO_3)_2 \cdot 6H_2O$) and 3.66 g of iron nitrate nonahydrate $Fe(NO_3)_3 \cdot 9H_2O$) were dissolved in distilled water (50 Ml) and stirred to form a first solution including a cobalt precursor and an iron precursor, and 1.47 g of bismuth nitrate pentahydrate ($Bi(NO_3)_2 \cdot 5H_2O$) was dissolved in distilled water (15 Ml) containing 3 Ml of nitric acid and stirred to form a second solution including a bismuth precursor. After bismuth nitrate pentahydrate was completely dissolved, the second solution was mixed with the first solution to form an acidic solution including a cobalt precursor, an iron precursor and a bismuth precursor. Further, 6.36 g of ammonium molybdate tetrahydrate (($NH_4)_6Mo_7O_{24} \cdot 4H_2O$) was dissolved in distilled water (100 Ml) to additionally form a third solution including a molybdenum precursor. Subsequently, the acidic solution was dropped into the third solution to form a mixed solution. The mixed solution was stirred at room temperature for 1 hour using a magnetic stirrer to be precipitated, and then the precipitated mixed solution was separated using a vacuum or centrifugal separator to obtain a solid sample. The obtained solid sample was dried at 175° C. for 24 hours. The dried solid sample was put into an electric furnace and then heat-treated at 475° C. to prepare a multi-component bismuth molybdate catalyst. The prepared multi-component bismuth molybdate catalyst was analyzed using X-ray diffraction (XRD) and inductively-coupled plasma atomic emission spectrometry (ICP-AES), and the results thereof are shown in FIG. 1 and Table 1. As shown in FIG. 1, it can be seen from the result of X-ray diffraction (XRD) analysis that the multi-component bismuth molybdate catalyst was prepared in the form of a mixed phase of β-$CoMoO_4$, $Fe_2(MoO_4)_3$, α-$Bi_2Mo_3O_{12}$, γ-$Bi_2MoO_6$ as reported in general documents, and it can be seen from the result of inductively-coupled plasma atomic emission spectrometry (ICP-AES) analysis that a desired amount of metal precursors was accurately coprecipitated within the allowable error range in analysis.

TABLE 1

Element composition ratio of a $Co_9Fe_3Bi_1Mo_{12}O_{51}$ catalyst prepared in Preparation Example 1 (relative ratio of other metal components to bismuth (Bi))

| Catalyst | Co | Fe | Bi | Mo |
|---|---|---|---|---|
| $Co_9Fe_3Bi_1Mo_{12}O_{51}$ | 9.0 | 3.2 | 1.0 | 11.4 |

Preparation Example 2

Preparation of Multi-Component Bismuth Molybdate Catalysts Including Manganese or Nickel as Metal Components Having Bivalent Cations In order to prepare multi-component bismuth molybdate catalysts including manganese or nickel as a metal component having bivalent cations, 7.83 g of manganese nitrate hexahydrate ($Mn(NO_3)_2 \cdot 6H_2O$) and 7.93 g of nickel nitrate hexahydrate ($Ni(NO_3)_2 \cdot 6H_2O$) were used. The multi-component bismuth molybdate catalysts were prepared under the same conditions as in Preparation Example 1, except the kind and amount of the precursor having bivalent cations. The prepared multi-component bismuth molybdate catalysts were analyzed using inductively-coupled plasma atomic emission spectrometry (ICP-AES). It can be seen from the ICP-AES analysis of the multi-component bismuth molybdate catalysts that a desired amount of metal precursors was accurately coprecipitated within the allowable error range in analysis. The results thereof are shown Table 2.

TABLE 2

| Catalyst | Metal having bivalent cations | Fe | Bi | Mo |
|---|---|---|---|---|
| $Mn_9Fe_3Bi_1Mo_{12}O_{51}$ | 9.1 (Mn) | 3.1 | 1.0 | 11.3 |
| $Ni_9Fe_3Bi_1Mo_{12}O_{51}$ | 8.7 (Ni) | 3.2 | 1.0 | 12.0 |

Comparative Preparation Example 1

Preparation of Multi-Component Bismuth Molybdate Catalysts Including Various Metal Components Having Bivalent Cations For comparison, multi-component bismuth molybdate catalysts including various metal components having bivalent cations were prepared. In order to prepare multi-component bismuth molybdate catalysts including magnesium, copper or zinc as a metal component having bivalent cations, 6.99 g of magnesium nitrate hexahydrate ($Mg(NO_3)_2 \cdot 6H_2O$), 6.59 g of copper nitrate trihydrate ($Cu(NO_3)_2 \cdot 6H_2O$) and 8.11 g of zinc nitrate hexahydrate ($Zn(NO_3)_2 \cdot 6H_2O$) were used. The multi-component bismuth molybdate catalysts were prepared under the same conditions as in Preparation Example 1, except the kind and amount of the precursor having bivalent cations. The prepared multi-component bismuth molybdate catalysts were analyzed using inductively-coupled plasma atomic emission spectrometry (ICP-AES). It can be seen from the ICP-AES analysis of the multi-component bismuth molybdate catalysts that a desired amount of metal precursors was accurately coprecipitated within the allowable error range in analysis. The results thereof are shown Table 3.

TABLE 3

Element composition ratios of multi-component bismuth molybdate catalysts prepared in Comparative Preparation Example 1 (relative ratios of other metal components to bismuth (Bi))

| Catalyst | Metal having bivalent cations | Fe | Bi | Mo |
|---|---|---|---|---|
| $Mg_9Fe_3Bi_1Mo_{12}O_{51}$ | 8.7 (Mg) | 3.0 | 1.0 | 11.5 |
| $Cu_9Fe_3Bi_1Mo_{12}O_{51}$ | 8.8 (Cu) | 2.8 | 1.0 | 11.8 |
| $Zn_9Fe_3Bi_1Mo_{12}O_{51}$ | 8.6 (Zn) | 3.1 | 1.0 | 12.0 |

Preparation Example 3

Preparation of a Zinc Ferrite ($ZnFe_2O_4$) Catalyst

Zinc chloride ($ZnCl_2$) was used as a zinc precursor, and iron chloride hexahydrate ($FeCl_3 \cdot 6H_2O$) was used as an iron precursor. In order to prepare a zinc ferrite catalyst, 1.42 g of zinc chloride and 5.61 g of iron chloride hexahydrate were dissolved in distilled water (100 Ml) and stirred to form an aqueous precursor solution. After the precursors were completely dissolved, the aqueous precursor solution was dropped into distilled water (100 Ml) and simultaneously an aqueous sodium hydroxide solution having a concentration of 3 M was added thereto such that the pH of a coprecipitation solution is 9, thus forming a mixed solution.

The mixed solution was sufficiently stirred at room temperature for 12 hours using a magnetic stirrer, and was then left at room temperature for 12 hours for phase separation, and thus the mixed solution was precipitated. The precipitated mixed solution was filtered using a vacuum filter to obtain a solid sample. The obtained solid sample was dried at 175° C. for 16 hours. The dried solid sample was put into an electric furnace and then heat-treated at 650° C. to prepare a single-phase zinc ferrite catalyst.

Figure 2:
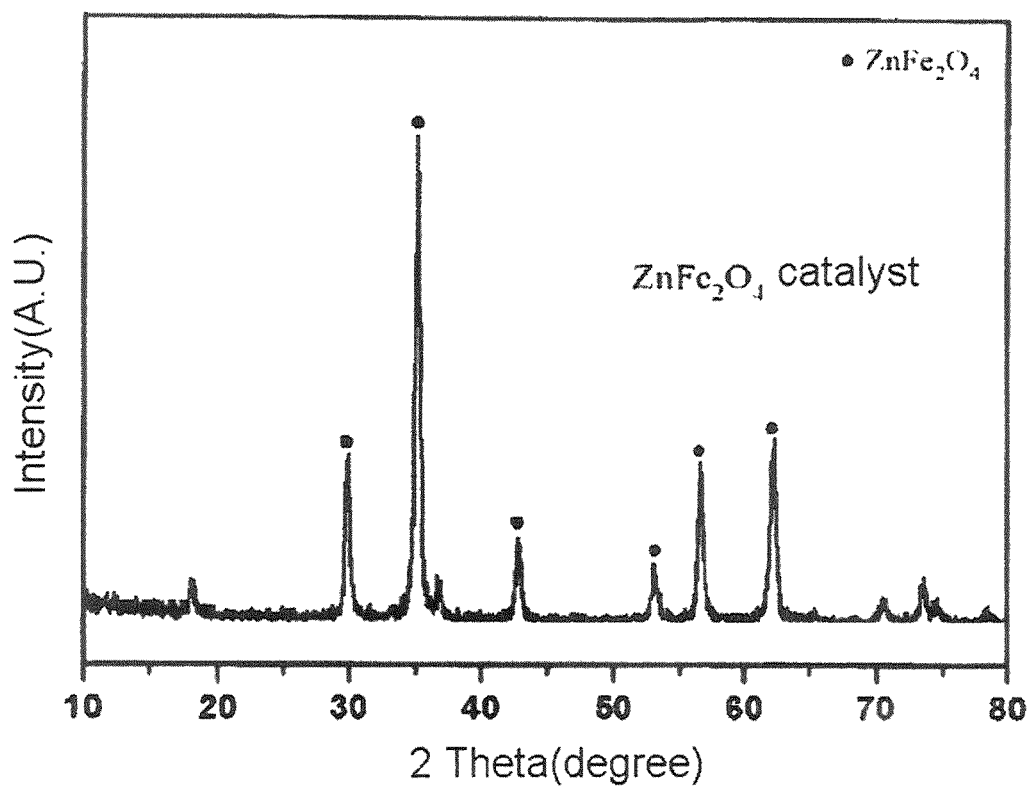
FIG. 2 is a graph showing the result of X-ray diffraction analysis of a zinc ferrite catalyst according to Preparation Example 3 of the present disclosure.

The prepared zinc ferrite catalyst was analyzed using X-ray diffraction (XRD) and inductively-coupled plasma atomic emission spectrometry (ICP-AES), and the results thereof are shown in FIG. 2 and Table 4. As shown in FIG. 2, it can be seen from the result of X-ray diffraction (XRD) analysis that the zinc ferrite catalyst was prepared in the form of a single phase, and it can be seen from the result of inductively-coupled plasma atomic emission spectrometry (ICP-AES) analysis that a desired amount of metal precursors was accurately coprecipitated within the allowable error range in analysis.

TABLE 4

Element composition ratio of a $ZnFe_2O_4$ catalyst prepared in Preparation Example 3 (relative ratio of other metal components to zinc (Zn))

| Catalyst | Fe | Zn |
| --- | --- | --- |
| $ZnFe_2O_4$ | 2.2 | 1 |

Comparative Preparation Example 2

Preparation of Zinc Ferrite ($ZnFe_2O_4$) Catalysts to the Change in pH of a Coprecipitation Solution For comparison, zinc ferrite catalysts were prepared under the same conditions as in Preparation Example 3, except that the PH of the precipitation solution was adjusted in a range of 3 to 5, 11 and 12. The phases of the prepared zinc ferrite catalyst were analyzed using X-ray diffraction (XRD). It can be seen from the XRD analysis that, when the pH of the precipitation solution was low (3~5), α-iron oxide (α-$Fe_2O_3$) catalysts, not zinc ferrite catalysts, were formed, and that, when the pH of the precipitation solution was high (11 and 12), single-phase zinc ferrite catalysts were formed.

Preparation Example 4

Configuration of a Continuous-Flow Dual-Bed Reactor Using a Multi-Component Bismuth Molybdate Catalyst and a Zinc Ferrite Catalyst A continuous-flow dual-bed reactor was configured such that synergetic effect can be obtained by combining the reaction characteristics of a multi-component bismuth molybdate catalyst to n-butene isomers with those of a zinc ferrite catalyst to n-butene isomers. Further, the continuous-flow dual-bed reactor using a multi-component bismuth molybdate catalyst and a zinc ferrite catalyst was configured by charging a multi-component bismuth molybdate catalyst into a conventional fixed-bed reactor to form a multi-component bismuth molybdate catalyst layer, applying powdered quartz onto the multi-component bismuth molybdate catalyst layer to form a quartz layer and then applying a zinc ferrite catalyst to the quartz layer to form a zinc ferrite catalyst layer or, conversely, by charging a zinc ferrite catalyst into a conventional fixed-bed reactor to form a zinc ferrite catalyst layer, applying powdered quartz onto the zinc ferrite catalyst layer to form a quartz layer and then applying a multi-component bismuth molybdate catalyst to the quartz layer to form a multi-component bismuth molybdate catalyst layer. Here, the two catalyst layers were designed such that they are physically separated from each other by the quartz layer and are independently operated, in this case, in order to compare the catalytic activity of the multi-component bismuth molybdate catalyst with that of the zinc ferrite catalyst, each of the two catalysts was used in an amount of 50 vol % the amount of catalyst used in a single catalytic reaction, thus equalizing the amount of the catalyst used in a single catalytic reaction with that of the catalyst used in a continuous dual catalytic reaction. Further, the quartz used to separate the two catalyst layers was at minimum in order to minimize the effects influencing the catalytic reactions.

Comparative Preparation Example 3

Preparation of a Composite Oxide Catalyst Including a Multi-Component Bismuth Molybdate and a Zinc Ferrite Catalyst Mechanically Mixed with Each Other In order to maximize the activity to the oxidative dehydrogenation reaction of n-butene by combining the reaction characteristics of a multi-component bismuth molybdate catalyst to n-butene isomers with those of a zinc ferrite catalyst to n-butene isomers, a composite oxide catalyst in which the two catalysts are mechanically mixed with each other was prepared. The multi-component bismuth molybdate catalyst prepared in Preparation Example 1 and the zinc ferrite catalyst prepared in Preparation Example 3 were pulverized and then mechanically mixed with each other to prepare a composite oxide catalyst. In the prepared composite oxide catalyst, the mixing ratio of the multi-component bismuth molybdate catalyst:the zinc ferrite catalyst was 50 vol %:50 vol %.

Experimental Example 1

Oxidative Dehydrogenation Traction of C4 Raffinate-3 or a C4 Mixture

The oxidative dehydrogenation reaction of n-butene was performed using the multi-component bismuth molybdate catalyst prepared in Preparation Example 1, the zinc ferrite catalyst prepared in Preparation Example 3, the dual-bed catalyst in which the two catalysts are sequentially applied, prepared in Preparation Example 4, and the composite oxide catalyst, in which the two catalysts are mechanically mixed with each other, prepared in Comparative Preparation Example 3. Here, a C4 mixture, air and steam were used as reactants, and a straight pyrex reactor was used as a reactor. In all experiments, in order to compare the catalytic activities of the catalysts to n-butene based on gas hourly space velocity (GHSV), the oxidative dehydrogenation reaction of n-butene was performed in a state in which the total amount of the catalysts is constant. The composition of the C4 mixture used as a reactant is shown in Table 5 below. The reactants were introduced into the straight pyrex reactor such that the ratio of n-butene:air:steam was 1:3.75:15. Steam, which was formed by vaporizing liquid water at a temperature of 200° C., was mixed with the C4 mixture and air, and was then introduced into the reactor. The amount of the C4 mixture and the amount of air were controlled by a mass flow controller, and the amount of steam was controlled by controlling the flow rate of liquid water using a syringe pump. The feed rate of each catalyst was set such that gas hourly space velocity (GHSV) was 475 h$^{-1}$ based on n-butene in the C4 mixture, and the reaction temperature was maintained such that the temperature of the catalyst layer of the straight pyrex reactor was 420° C. The reaction product obtained by the oxidative dehydrogenation reaction of n-butene was analyzed using gas chromatography. As a result, it was found that the reaction product includes carbon dioxide by perfect oxidation, side products by cracking, n-butane, and the like in addition to 1,3-butadiene. The conversion ratio of n-butene, selectivity of 1,3-butadiene and yield of 1,3-butadiene due to the oxidative dehydrogenation of n-butene on the multi-component bismuth molybdate catalyst are calculated by the following Mathematical Equations 1, 2 and 3.

$$\text{Conversion ratio (\%)} = \frac{\text{moles of reacted } n\text{-butene}}{\text{moles of supplied } n\text{-butene}} \times 100 \quad \text{Mathematical Equation 1}$$

$$\text{Selectivity (\%)} = \frac{\text{moles of 1,3-butadiene formed}}{\text{moles of reacted } n\text{-butene}} \times 100 \quad \text{Mathematical Equation 2}$$

$$\text{Yield (\%)} = \frac{\text{moles of 1,3-butadiene formed}}{\text{moles of supplied } n\text{-butene}} \times 100 \quad \text{Mathematical Equation 3}$$

Example 1

Reaction Activities of Multi-Comment Bismuth Molybdate Catalysts and a Zinc Ferrite Catalyst The oxidative dehydrogenation reaction of a C4 mixture was performed in the same manner as in Experimental Example 1 using the multi-component bismuth molybdate catalysts prepared in Preparation Examples 1 and 2 and the zinc ferrite catalyst prepared in Preparation. Example 3, and the results thereof are shown in Table 6 and FIG. 3. It can be seen from Table 6 and FIG. 3 that the yield of 1,3-butadiene in the oxidative dehydrogenation reaction of n-butene using the zinc ferrite catalyst is higher than the yield of 1,3-butadiene in the oxidative dehydrogenation reaction of 1-butene using the multi-component bismuth molybdate catalysts. Further, since multi-component bismuth molybdate-based catalysts and ferrite-based catalysts, which have different crystal structures, have different sites for adsorbing and activating n-butene, and the characteristic of oxygen in lattices thereof are different from each other, it is expected that the reaction activities of the catalysts to the oxidative dehydrogenation reaction of n-butene be different from each other.

TABLE 6

Reaction activity of multi-component bismuth molybdate catalysts and a zinc ferrite catalyst

| Catalyst | Conversion ratio of n-butene (%) | Selectivity of 1,3-butadiene (%) | Yield of 1,3-butadiene (%) |
|---|---|---|---|
| Multi-component bismuth molybdate catalyst (Co$_9$Fe$_3$Bi$_1$Mo$_{12}$O$_{51}$) | 66.9 | 90.7 | 60.6 |
| Mn$_9$Fe$_3$Bi$_1$Mo$_{12}$O$_{51}$ | 54.7 | 88.8 | 48.6 |
| Ni$_9$Fe$_3$Bi$_1$Mo$_{12}$O$_{51}$ | 58.8 | 89.7 | 52.7 |
| Zinc ferrite catalyst (ZnFe$_2$O$_4$) | 78.4 | 92.3 | 72.3 |

TABLE 5

Composition of C4 mixture used as reactant

| Composition | Molecular formula | wt % |
|---|---|---|
| i-butane | C$_4$H$_{10}$ | 0.07 |
| n-butane | C$_4$H$_{10}$ | 41.57 |
| methyl cyclopropane | C$_4$H$_8$ | 0.09 |
| trans-2-butene | C$_4$H$_8$ | 33.94 |
| 1-butene | C$_4$H$_8$ | 7.52 |
| isobutylene | C$_4$H$_8$ | 0.02 |
| cis-2-butene | C$_4$H$_8$ | 16.48 |
| cyclobutane | C$_4$H$_8$ | 0.29 |
| i-pentane | C$_5$H$_{12}$ | 0.02 |
| Sum | | 100 |

Figure 4:
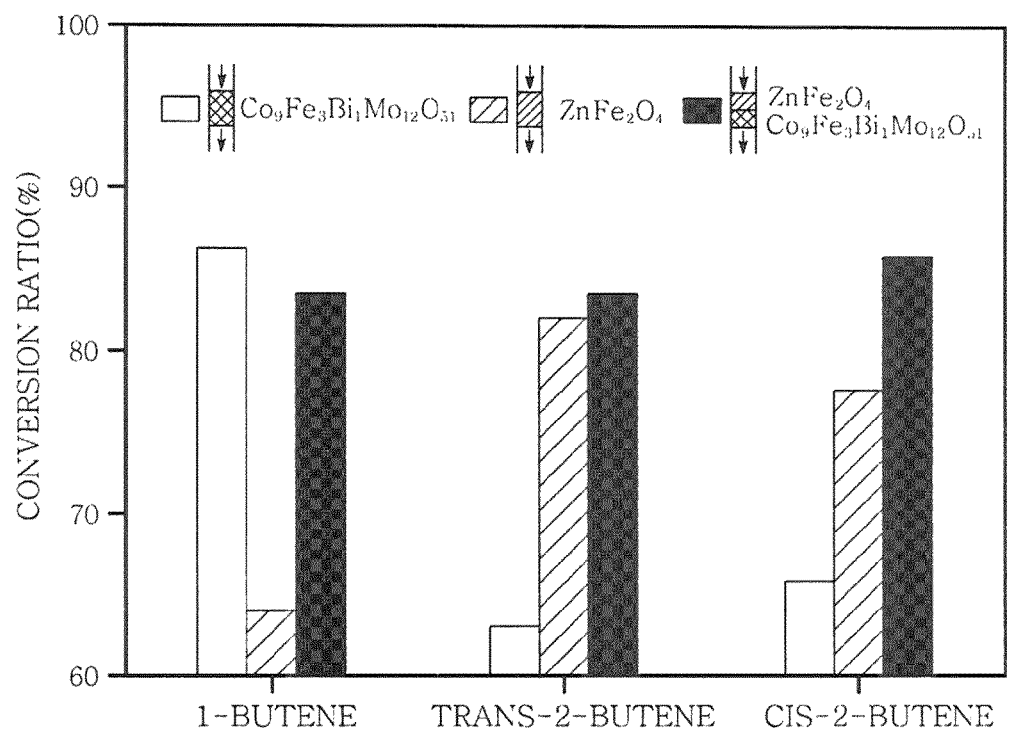
FIG. 4 is a graph showing the changes in reaction activity to n-butene isomers in a continuous-flow dual-bed reactor according to Examples 1 and 2 of the present disclosure.

It is remarkably attended that the reaction activity of a multi-component bismuth molybdate catalyst to n-butene isomers in a C4 mixture is different from that of a zinc ferrite catalyst to n-butene isomers in a C4 mixture. The results thereof are shown in Table 7 and FIG. 4. The reaction activities of the catalysts are calculated by the following Mathematical Equations 4, 5 and 6, respectively. It can be seen from Table 7 that the reaction activity of the multi-component bismuth molybdate catalyst to 1-butene is higher than that of the multi-component bismuth catalyst to 2-butene (trans-2-butene or cis-2-butene), but that the reaction activity of the zinc ferrite catalyst to 2-butene (trans-2-butene or cis-2-butene) is higher than that of the zinc ferrite catalyst to 1-butene. Therefore, when the oxidative dehydrogenation reaction of n-butene is performed using both the multi-component bismuth catalyst and the zinc ferrite catalyst, it is expected that the reaction activity of the two catalysts to n-butene isomers is increased due to the synergetic effect of the two catalysts, thus increasing the yield of 1,3-butadiene.

Therefore, as described above, in order to obtain the synergetic effect of the two catalysts, in Comparative Example 3, the oxidative dehydrogenation reaction of n-butene was conducted using the composite oxide catalyst formed by mechanically mixing the two catalysts, and, in Example 2, the oxidative dehydrogenation reaction of n-butene was conducted using the continuous-flow dual-bed reactor.

TABLE 7

Reaction activity of a multi-component bismuth molybdate catalyst to n-butene isomers and reaction activity of a zinc ferrite catalyst to n-butene isomers

| Catalyst | Conversion ratio of 1-butene (%) | Conversion ratio of trans-2-butene (%) | Conversion ratio of cis-2-butene (%) |
|---|---|---|---|
| Multi-component bismuth molybdate catalyst ($Co_9Fe_3Bi_1Mo_{12}O_{51}$) | 86.3 | 63.0 | 65.8 |
| Zinc ferrite catalyst ($ZnFe_2O_4$) | 64.0 | 82.0 | 77.6 |

Mathematical Equation 4
$$\text{1-butene conversion ratio (\%)} = \frac{\text{moles of reacted 1-butene}}{\text{moles of 1-butene included in supplied } C4 \text{ mixture}} \times 100$$

Mathematical Equation 5
$$\text{trans-2-butene conversion ratio (\%)} = \frac{\text{moles of reacted trans-2-butene}}{\text{moles of trans-2-butene included in supplied } C4 \text{ mixture}} \times 100$$

Mathematical Equation 6
$$\text{cis-2-butene conversion ratio (\%)} = \frac{\text{moles of reacted cis-2-butene}}{\text{moles of cis-2-butene included in supplied } C4 \text{ mixture}} \times 100$$

Comparative Example 1

Reaction Activities of Multi-Component Bismuth Molybdate Catalysts Including Metal Components Having Various Bivalent Cations The oxidative dehydrogenation reaction of a C4 mixture was performed in the same manner as in Experimental Example 1 using the multi-component bismuth molybdate catalysts including metal components having different bivalent cations, prepared in Comparative Preparation Example 1, and the results thereof are shown in Table 8. The phases of the catalysts are changed depending on the kinds of the metal components, so that the properties of the surfaces of the catalysts and the characteristics of oxygen in the lattices of the catalysts are changed, with the result that the catalysts exhibit different reaction activities, respectively. Comparing Table 6 with Table 8, it can be seen that the multi-component bismuth molybdate catalyst including cobalt as bivalent cations exhibits the highest reaction activity in the oxidative hydrogenation reaction of n-butene. Therefore, it is determined that a $Co_9Fe_3Bi_1Mo_{12}O_{51}$ catalyst is most suitable to be used as the multi-component bismuth molybdate catalyst constituting the continuous-flow dual-bed reactor of the present disclosure.

TABLE 8

Reaction activities of multi-component bismuth molybdate catalysts including metal components having different bivalent cations

| Catalyst | Conversion ratio of n-butene (%) | Selectivity of 1,3-butadiene (%) | Yield of 1,3-butadiene (%) |
|---|---|---|---|
| $Mg_9Fe_3Bi_1Mo_{12}O_{51}$ | 39.0 | 81.4 | 31.8 |
| $Cu_9Fe_3Bi_1Mo_{12}O_{51}$ | 12.6 | 42.9 | 5.4 |
| $Zn_9Fe_3Bi_1Mo_{12}O_{51}$ | 42.9 | 92.5 | 39.7 |

Comparative Example 2

Reaction Activities of Zinc Ferrite Catalysts Prepared Using Various Coprecipitation Solutions Having Different pHs The oxidative dehydrogenation reaction of a C4 mixture was performed in the same manner as in Experimental Example 1 using the zinc ferrite catalysts prepared using various coprecipitation solutions having different pHs, prepared in Comparative Preparation Example 2, and the results thereof are shown in Table 9. The phases of the catalysts are changed depending on the pH of the coprecipitation solution, so that the properties of the surfaces of the catalysts and the characteristics of oxygen in the lattices of the catalysts are changed, with the result that the catalysts exhibit different reaction activities, respectively. Comparing Table 6 with Table 9, it can be seen that a zinc ferrite catalyst prepared using a coprecipitation solution having a pH of 9 exhibits the highest reaction activity in the oxidative hydrogenation reaction of n-butene. Therefore, it is determined that the zinc ferrite catalyst prepared using a coprecipitation solution having a pH of 9 is most suitable to be used as the multi-component bismuth molybdate catalyst constituting the continuous-flow dual-bed reactor of the present disclosure.

TABLE 9

Reaction activities of zinc ferrite catalysts prepared using various coprecipitation solutions having different pHs

| pH at the time of preparing a catalyst | Conversion ratio of n-butene (%) | Selectivity of 1,3-butadiene (%) | Yield of 1,3-butadiene (%) |
|---|---|---|---|
| 3 | 17.0 | 45.0 | 7.7 |
| 4 | 30.4 | 68.7 | 20.9 |
| 5 | 42.8 | 77.0 | 32.9 |
| 11 | 29.7 | 68.6 | 20.3 |
| 12 | 15.6 | 27.7 | 4.3 |

Comparative Example 3

Figure 3:
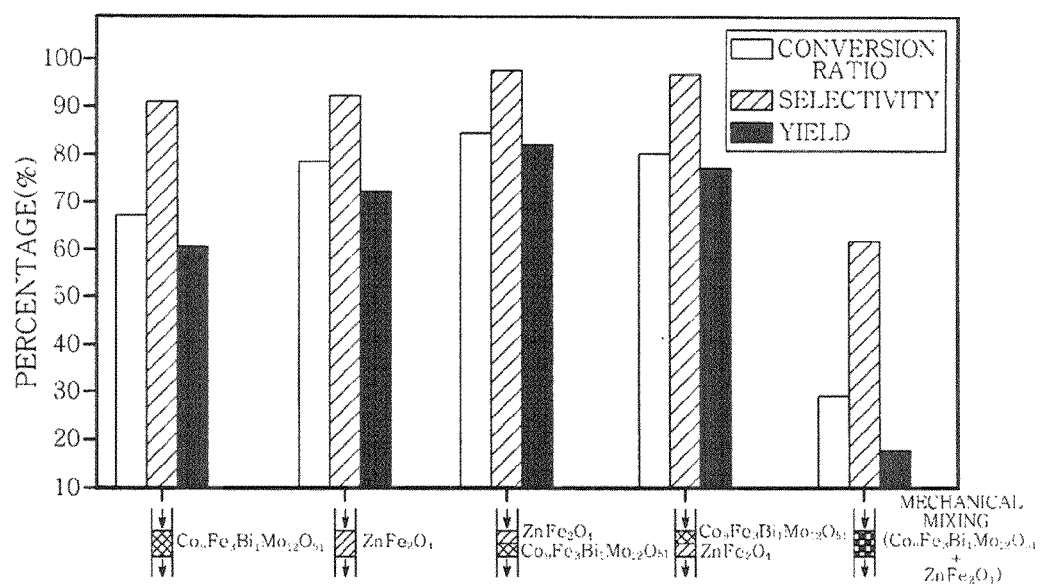
FIG. 3 is a graph comparing the reaction results of Example 1, Example 2 and Comparative Example 3.

Reaction Activity of a Composite Oxide Catalyst Including a Multi-Component Bismuth Molybdate Catalyst and a Zinc Ferrite Catalyst Mechanically Mixed with Each Other The oxidative dehydrogenation reaction of a C4 mixture was performed in the same manner as in Experimental Example 1 using the composite oxide catalyst including a multi-component bismuth molybdate catalyst and a zinc ferrite catalyst mechanically mixed with each other, prepared in Comparative Preparation Example 3, and the results thereof are shown in Table 10 and FIG. 3. The reaction activity of the composite oxide catalyst was greatly decreased compared to when the oxidative dehydrogenation reaction of the C4 mixture was performed using each of the multi-component bismuth molybdate catalyst and the zinc ferrite catalyst (refer to Example 1 and Table 6). The reason for this is determined that these two catalysts come into contact with each other, so that the catalytic actions of the two catalysts in the oxidative dehydrogenation reaction of n-butene interfere with each other, thereby decreasing the reaction activity thereof to n-butene.

TABLE 10

Reaction activity of a composite oxide catalyst including a multi-component bismuth molybdate catalyst and a zinc ferrite catalyst mechanically mixed with each other

| Catalyst | Conversion ratio of n-butene (%) | Selectivity of 1,3-butadiene (%) | Yield of 1,3-butadiene (%) |
|---|---|---|---|
| Composite oxide catalyst (multicomponent bismuth molybdate + zinc ferrite) | 28.9 | 61.7 | 17.8 |

Example 2

Reaction Activities of a Multi-Component Catalyst and a Zinc Ferrite Catalyst Charged in a Continuous-Flow Dual-Bed Reactor in the Oxidative Dehydrogenation of n-Butene The oxidative dehydrogenation reaction of a C4 mixture was performed in the same manner as in Experimental Example 1 using the multi-component bismuth molybdate catalyst prepared in Preparation Example 1 and the zinc ferrite catalyst prepared in Preparation Example 3, and the results thereof are shown in Table 11 and FIG. 3. As shown in Table 11, when the oxidative dehydrogenation reaction of n-butene was first performed using a zinc ferrite catalyst, that is, when the zinc ferrite catalyst was used in the oxidative dehydrogenation reaction of n-butene, the yield of 1,3-butadiene was increased. In contrast, when the oxidative dehydrogenation reaction of n-butene was first performed using a multi-component bismuth molybdate catalyst, that is, when the multi-component bismuth molybdate catalyst was used in the oxidative dehydrogenation reaction of n-butene, the yield of 1,3-butadiene was decreased. It is determined that the change in yield of 1,3-butadiene according to the order of disposing the two catalysts was attributable to the composition ratio of n-butene isomers. That is, it is determined that, since the C4 mixture used in the present includes more 2-butene (50.4 wt %) than 1-butene (7.5 wt %), when the oxidative dehydrogenation reaction of n-butene was first performed using the zinc ferrite catalyst having excellent reaction activity thereof to 2-butene, the yield of 1,3-butadiene was increased. On the contrary, when the amount of 1-butene in the C4 mixture Is increased, when the oxidative dehydrogenation reaction of n-butene was first performed using the multi-component bismuth molybdate catalyst having excellent reaction activity thereof to 1-butene, it is expected that the synergetic effect of the two catalyst is further improved. In the present disclosure, when the oxidative dehydrogenation reaction of n-butene was first performed using the zinc ferrite catalyst, that is, when the zinc ferrite catalyst was first brought into contact with reactants, higher yield of 1,3-butadiene could be obtained. However, since the composition of the reactants can be variously changed, the present disclosure is not limited to the order of disposing the catalysts.

TABLE 11

Reaction activities of a multi-component catalyst and a zinc ferrite catalyst charged in a continuous-flow dual-bed reactor in the oxidative dehydrogenation of n-butene

| Catalyst | Positions of catalysts in continuous-flow dual-bed reactor (reaction first occurs on upper layer) | Conversion ratio of n-butene (%) | Selectivity of 1,3-butadiene (%) | Yield of 1,3-butadiene (%) |
|---|---|---|---|---|
| multicomponent bismuth molybdate + zinc ferrite | upper layer: multicomponent bismuth molybdate lower layer: zinc ferrite | 80.1 | 96.6 | 77.4 |
| zinc ferrite + multicomponent bismuth molybdate | upper layer: zinc ferrite lower layer: multicomponent bismuth molybdate | 84.2 | 97.5 | 82.1 |

In brief, when the oxidative dehydrogenation reaction of n-butene was performed using the continuous dual-bed reactor provided with the two catalysts, a higher yield of 1,3-butadiene was obtained compared to when the oxidative dehydrogenation reaction of n-butene was performed using a single catalyst. From the results, it can be seen that the characteristics of the multi-component bismuth molybdate catalyst having high reaction activity thereof to 1-butene of the n-butene isomers are combined with those of the zinc ferrite catalyst having high reaction activity thereof to 2-butene of the n-butene isomers by the continuous-flow dual-bed reactor, so that the reaction activities of the catalysts to all of the n-butene isomers in oxidative dehydrogenation reaction are increased, thereby increasing the yield of 1,3-butadiene. In the continuous-flow dual-bed reactor, when the oxidative dehydrogenation reaction of n-butene was first performed using the zinc ferrite catalyst, that is, when the oxidative dehydrogenation reaction of n-butene was first performed in a state in which the zinc ferrite catalyst is charged in the upper layer and the multi-component bismuth molybdate catalyst is charged in the lower layer, the reaction activities of the catalysts to the n-butene isomers in the C4 mixture, calculated by Mathematical Equations 4, 5 and 6, are shown in Table 12 and FIG. 4. Observing the changes in reaction activity of the catalysts to the n-butene isomer, shown in FIG. 4, it can be clearly seen that the synergetic effect of the two catalysts in the continuous-flow dual-bed reactor was further improved. That is, it can be seen that, when the oxidative dehydrogenation reaction of n-butene was performed in continuous-flow dual-bed reactor, the reaction activities of the catalysts to the n-butene isomers are improved compared to when the oxidative dehydrogenation reaction of n-butene was performed using the catalysts separately, thus increasing the yield of 1,3-butadiene,

TABLE 12

Reaction activity of the continuous-flow dual bed reactor to each of n-butene isomers

| Order of catalysts contacting reactants | Conversion ratio of 1-butene (%) | Conversion ratio of trans-2-butene (%) | Conversion ratio of cis-2-butene (%) |
|---|---|---|---|
| zinc ferrite + multi-component bismuth molybdate | 83.6 | 83.6 | 85.9 |

The foregoing examples are provided merely for the purpose of explanation and are in no way to be construed as limiting. While reference to various embodiments are shown, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

The invention claimed is:

1. A method of producing 1,3 butadiene using a continuous-flow dual bed reactor, comprising:
   a) charging the continuous-flow dual bed reactor with a bismuth molybdate-based first catalyst and a ferrite-based second catalyst layer to form a first catalyst layer and a second catalyst layer such that a quartz layer is disposed between the first and second catalyst layers to separate the first and second catalyst layers;
   b) passing a reactant including a C4 mixture containing n-butene, air and steam through the catalyst layers of the continuous-flow dual bed reactor to conduct an oxidative dehydrogenation reaction; and
   c) obtaining 1,3-butadiene by the oxidative dehydrogenation reaction.

2. The method according to claim 1, wherein the C4 mixture includes 0.5~50 wt % of n-butane, 40~99 wt % of n-butene, and 0.5~10 wt % of residual C4 compounds.

3. The method according to claim 1, wherein the reactant includes n-butene, air and steam such that a ratio of n-butene:air:steam is 1:0.5~10:1~50.

4. The method according to claim 1, wherein, in b), the oxidative dehydrogenation reaction is conducted at a reaction temperature of 300~600° C. and a gas hourly space velocity (GHSV) of 50~5000 h−1.

5. The method according to claim 1, wherein the first catalyst is a bismuth molybdate catalyst including four kinds of metals, and
   wherein the bismuth molybdate catalyst is prepared by:
   a1) providing a first solution including a precursor of a metal having bivalent cations, selected from the group consisting of manganese, cobalt and nickel, an iron precursor, and a bismuth precursor,
   b1) providing a second solution in which a molybdenum precursor is dissolved;
   c1) dripping the first solution into the second solution to form a coprecipitation solution;

d1) stirring the coprecipitation solution for 1~2 hours and then removing moisture therefrom to obtain a solid sample; and e1) drying the solid sample at 150~200° C. and then heat-treating the dried solid sample at 400~600° C.

6. The method according to claim 5, wherein the metal having bivalent cations is cobalt.

7. The method according to claim 5, wherein a molar ratio of the metal precursor:the iron precursor:the bismuth precursor:the molybdenum precursor is 7~10:2~4:1:5~20.

8. The method according to claim 5, wherein, in a1), the metal precursor is manganese nitrate, cobalt nitrate or nickel nitrate, the iron precursor is iron nitrate, and the bismuth precursor is bismuth nitrate.

9. The method according to claim 5, wherein, in b1), the molybdenum precursor is ammonium molybdate.

10. The method according to claim 1, wherein the second catalyst is a zinc ferrite catalyst, and wherein the zinc ferrite catalyst is prepared by:

a2) dissolving a zinc precursor and an iron precursor in distilled water to form an aqueous precursor solution;

b2) mixing a sodium hydroxide solution having a molar concentration of 1.5~4.0 M with the aqueous precursor solution to form a mixed solution having a pH of 6~10;

c2) filtering the mixed solution to obtain a solid catalyst;

d2) drying the solid catalyst at 70~200° C.; and e2) heat-treating the dried solid catalyst at 350~800° C.

11. The method according to claim 10, wherein, in a2), the ratio of number of zinc atoms of the zinc precursor and number of iron atoms of the iron precursor is 1.5~2.5.

12. The method according to claim 10, wherein, in a2), the zinc precursor is zinc chloride or zinc nitrate, and the iron precursor is iron chloride or iron nitrate.

13. The method according to claim 1, wherein, when the C4 mixture includes more 1-butene than 2-butene, in a), the first catalyst layer, the quartz layer and the second catalyst layer are sequentially disposed downward.

14. The method according to claim 1, wherein, when the C4 mixture includes more 2-butene than 1-butene, in a), the second catalyst layer, the quartz layer and the first catalyst layer are sequentially disposed downward.

* * * * *